United States Patent [19]

Evans et al.

[11] 4,134,993

[45] Jan. 16, 1979

[54] BENZOPHENONE DERIVATIVES

[75] Inventors: Delme Evans, Chalfont St. Peter; John C. Saunders, Maidenhead; William R. N. Williamson, Slough, all of England

[73] Assignee: Eli Lilly and Company, Indianapolis, Ind.

[21] Appl. No.: 840,882

[22] Filed: Oct. 11, 1977

[30] Foreign Application Priority Data

Oct. 14, 1976 [GB] United Kingdom ............... 42682/76

[51] Int. Cl.$^2$ ........................ A01N 9/24; C07G 49/76
[52] U.S. Cl. ..................................... 424/331; 260/591
[58] Field of Search ......................... 260/591; 424/331

[56] References Cited

U.S. PATENT DOCUMENTS

| | | | |
|---|---|---|---|
| 3,954,875 | 5/1976 | Swithenbank et al. | 424/331 |
| 3,957,885 | 5/1976 | Karrer et al. | 424/331 |
| 4,027,040 | 5/1977 | Deraedt et al. | 424/331 |

FOREIGN PATENT DOCUMENTS

| | | | |
|---|---|---|---|
| 560324 | 7/1958 | Canada | 260/591 |
| 1091182 | 1/1965 | United Kingdom | 260/591 |

OTHER PUBLICATIONS

Hnevsova-Seidlova et al., Chem. Abst., vol. #78539 (1963).
Miraslov et al., Chem. Abst., vol. 61, #5568a.
Gibson et al., J. Chem. Soc., Perkin Trans. 1, (2), pp. 155–160 (1975).

*Primary Examiner*—James O. Thomas, Jr.
*Assistant Examiner*—James H. Reamer
*Attorney, Agent, or Firm*—Kathleen R. S. Page; Arthur R. Whale

[57] ABSTRACT

Novel benzophenone derivatives having anti-allergy activity, and pharmaceutical formulations and methods of treatment utilizing benzophenone derivatives.

10 Claims, No Drawings

BENZOPHENONE DERIVATIVES

This invention relates to a class of novel benzophenone derivatives, to methods of preparing such derivatives and to pharmaceutical formulations.

2'-and 3'-Chloro-5-methyl-2-(methylthio) benzophenones have been described by Gibson et al, J. Chem.-Soc.Perkin Trans. 1(1975), (2) 155-60. However no utility, and in particular no pharmacological activity, is disclosed therein for these compounds.

According to the present invention there is provided a benzophenone derivative of formula (I):

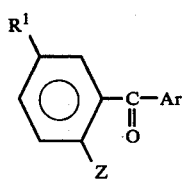
(I)

wherein $R^1$ is $C_{1-4}$ alkyl, Z is SH, $SR^2$, $SOR^2$ or $SO_2R^2$ and Ar is a phenyl group optionally substituted by from one to three groups selected from halogen and methyl, provided that when Z is $-SR^2$, $R^2$ is methyl and Ar is ortho-or meta-chlorophenyl, $R^1$ is $C_{2-4}$ alkyl.

The invention also provides a pharmaceutical formulation comprising an active ingredient in association with a pharmaceutically acceptable carrier therefor, the active ingredient being a compound of formula (I) as defined above, 2'-chloro-5-methyl-2-(methylthio) benzophenone or 3'-chloro-5-methyl-2-(methylthio) benzophenone; and a method of making such a pharmaceutical formulation which comprises bringing such an active ingredient into association with a pharmaceutically acceptable carrier therefor.

In accordance with the invention there is further provided a method of treating an animal suffering from or susceptible to an allergic condition, and particularly a method of treating immediate hypersensitivity diseases such as asthma in animals, including humans, which method comprises administering to the animal a therapeutically effective amount of a compound of formula (I) as defined above, or 2'-or 3'-chloro-5-methyl-2-(methylthio) benzophenone.

Preferred compounds of formula (I) are those having one or more of the following features:
(a) $R^1$ is $C_{2-4}$ alkyl,
(b) $R^1$ is ethyl,
(c) Z is $SR^2$,
(d) Z is $SOR^2$,
(e) Z is $SCH_3$,
(f) Z is $SOCH_3$,
(g) Ar is phenyl optionally singly substituted by halogen or methyl,
(h) Ar is unsubstituted phenyl,
(i) Ar is p-chlorophenyl,
(j) Ar is p-fluorophenyl,
(k) Ar is p-methylphenyl, Particularly preferred compounds have features (a), (c) and (g); or (a), (d) and (g); and more especially preferred are compounds having features (b), (e) and (h); (b), (e) and (i); (b), (e) and (j); (b), (f) and (h); (b) (f) and (i); (b), (f) and (j); and (b), (f) and (k).

The present invention also provides a method of preparing a compound of formula (I) as defined above comprising effecting an acylation reaction in the presence of a Lewis acid between a compound of formula:

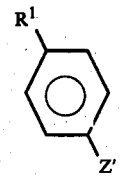

and a compound of formula:

Ar COCl wherein $R^1$ and Ar are as defined above and Z' is $SR^2$, $NH_2$ or $NHR^3$ where $R^3$ is an amine protecting group such as $COR^2$ or COAr, followed by hydrolysis of the resulting complex and, when Z' is $NH_2$ or $NHR^3$, by converting the $NH_2$ or $NHR^3$ group to SH, $SR^2$, $SOR^2$ or $SO_2R^2$ via a diazonium intermediate, and optionally oxidising, for example with $H_2O_2$, to convert $SR^2$ to $SOR^2$ or $SO_2R^2$.

The above acylation reaction is an example of the well-known Friedel-Crafts acylation reaction and is carried out under conventional Friedel-Crafts acylating conditions. The Lewis acid is advantageously $AlCl_3$.

The benzophenone derivatives of the present invention are either useful in the prophylactic treatment of immediate hypersensitivity conditions including asthma and in the alleviation of status asthmaticus in humans. The compounds have low toxicity.

The compounds or compositions of the present invention may be administered by various routes and for this purpose may be formulated in a variety of forms. Thus the compounds or compositions may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders absorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administeration) of a compound of formula (I).

Dosages of from 0.5 to 80 mg/kg per day, preferably 2 to 20 mg/kg, of active ingredient may be administered. It will however, readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

In this specification, the expression "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or more units are normally required for a single therapeutic administration or that, in the case of severable units such as scored tablets at least one fraction such as a half or a quarter of a severable unit is required for a single therapeutic administration.

The formulations of the present invention normally will consist of at least one compound of formula (I) associated with a pharmaceutically acceptable carrier therefor, i.e. mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material, which serves as a vehicle, excipient or medium for the active therapeutic substance.

Some examples of the diluents or carriers which may be employed in the pharmacuetical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatine, syrup B.P., methyl cellulose, polyoxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminum, magnesium or calcium stearates, talc or mineral oil.

The invention will be further understood from the following examples.

EXAMPLE 1

5-Ethyl-4'-methyl-2-(methylthio)benzophenone

Aluminum chloride (10.8g) was added in portions to an ice-cooled, stirred solution of 4-(ethyl)thioanisole (12.3g) and 4-methylbenzoyl chloride (12.5g) in 1,2-dichloroethane (60 ml). The mixture was allowed to come to ambient temperature and was stirred overnight. It was then poured into a mixture of concentrated hydrochloric acid (about 100 ml) and ice (200 gm), which mixture was extracted with chloroform (3 × 100 ml), and the combined organic fractions were washed with 10% w/v aqueous sodium carbonate solution (2 × 100 ml) and water (100 ml), dried over magnesium sulphate and evaporated to leave the crude product as an oil. This oil was distilled twice to give the title compound as a clear oil (bp 152°–154° C./0.01 mm). The structure was confirmed by NMR.

Microanalysis: $C_{17} H_{18}$ OS Calculated: C:75.5%, H:6.7%, S:11.9%. Found: C:75.8%, H:6.8%, S:11.9%.

EXAMPLES 2 to 4

Using the method of Examples 1 there were also prepared: 5-ethyl-4'-fluoro-2-(methylthio)benzophenone, bp 145°–148° C./0.05mm.

Microanalysis: $C_{16} H_{15}$ FOS Calculated: C:70.1%, H:5.5%, F:6.9%, S:11.7%. Found: C:70.1%, H:5.6%, F:7.1%, S:11.4%. 4'-chloro-5-ethyl-2-(methylthio)benzophenone, bp 150°–155° C./0.07 mm, Microanalysis: $C_{16} H_{15}$ ClOS Calculated: C:66.1%, H:5.2%, Cl:12.2%, S:11.0%. Found: C:66.0%, H:5.3%, Cl:12.4%, S:11.0%. 5-ethyl-2(methylthio)benzophenone, bp 140°–142° C./0.08mm, Microanalysis: $C_{16} H_{16}$ OS Calculated: C:75.0%, H:6.3%. Found: C:74.5%, H:6.3%.

EXAMPLE 5

5-Ethyl-4'-fluoro-2-(methylsulphonyl)benzophenone

5-Ethyl-4'-fluoro-2-(methylthio)benzophenone (see Example 2) (2.74g, 0.01 mol) and 30% hydrogen peroxide solution (3.4 ml, 0.03 mol) were refluxed together in acetic acid (20 ml) for three hours. The resulting mixture was cooled and then poured into ice/water to give a solid which was collected and recrystallised twice from a mixture of hexane and chloroform and purified by preparative thin layer chromatography using a 3:1 mixture (V/V) of chloroform and ether to yield the pure title compound (1 g), mp 145°–147° C.

Microanalysis: $C_{16} H_{15}$ $FO_3S$ Calculated: C:62.73%; H:4.94%; F:6.2%; S:10.46%. Found: C:63.01%; H:4.78%; F:6.47%; S:10.26%.

EXAMPLES 6 and 7

Using the method of Examples 5 there was also prepared: 4'-Chloro-5-ethyl-2-(methylsulphonyl)benzophenone, mp 124°–127° C., Microanalysis: $C_{16}H_{15}$ Cl $O_3S$ Calculated: C:59.53%; H:4.68%; Cl:10.98%; S:9.93%. Found: C:59.79%; H:4.68%; Cl:11.18%; S:9.85%. 5-Ethyl-4'-methyl-2-(methylsulphonyl)benzophenone, mp 92°–95° C.

Microanalysis: $C_{17} H_{18}$ $O_3S$ Calculated: C:67.52%; H:6.0%; S:10.6%. Found: C:67.79%; H:5.97%; S:10.46%.

EXAMPLES 8 to 10

The following methylsulphinyl compounds were prepared by following the procedure of Example 5 using half the quantity of hydrogen peroxide per mole of methylthio starting compound used in that Example. 5-Ethyl-4'-fluoro-2-(methylsulphinyl)benzophenone, mp 79°–80° C.

Microanalysis: $C_{16} H_{15}$ $FO_2S$ Calculated: C:66.19%; H:5.2%; F:6.24%; S:11.04%. Found: C:66.45%; H:5.18%; F:6.52%; S:10.96%. 4'-Chloro-5-ethyl-2-(methylsulphinyl)benzophenone, mp 90°–92° C.

Microanalysis: $C_{16} H_{15}$ $ClO_2S$ Calculated: C:62.64%; H:4.93%; Cl:11.55%; S:10.45%. Found: C:62.87%; H:4.96%; Cl:11.76%; S:10.29%. 5-Ethyl-4'-methyl-2-(methylsulphinyl)benzophenone, mp 74°–76° C.

Microanalysis: $C_{17} H_{18}$ $O_2S$ Calculated: C:71.3%; H:6.34%; S:11.19%. Found: C:71.59%; H:6.1%; S:10.93%.

We claim:

1. A method of treating asthma which comprises administering to an animal suffering from or susceptible to asthma a chemotherapeutically effective amount of a compound of formula (I)

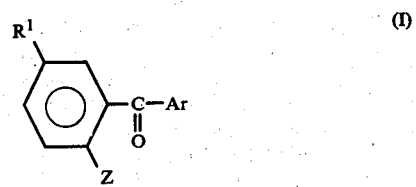

wherein $R^1$ is $C_{1-4}$ alkyl; Z is SH, $SR^2$, $SOR^2$ or $SO_2R^2$, where $R^2$ is $C_{1-4}$ alkyl; and Ar is phenyl or phenyl substituted by from one to three groups selected from halogen and methyl.

2. A pharmaceutical formulation consisting essentially of a therapeutically effective amount of an active ingredient being a compound of formula (I):

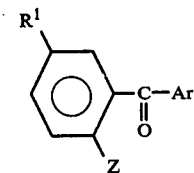

(I)

wherein $R^1$ is $C_{1-4}$ alkyl; Z is SH, $SR^2$, $SOR^2$ or $SO_2R^2$, where $R^2$ is $C_{1-4}$ alkyl; and Ar is phenyl or phenyl substituted by from one to three groups selected from halogen and methyl, associated with a pharmaceutically acceptable carrier therefor.

3. The formulation of claim 2 wherein the compound of formula (I) is 5-ethyl-4'-methyl-2-(methylthio)benzophenone.

4. The formulation of claim 2 wherein the compound of formula (I) is 5-ethyl-4'-fluoro-2-(methylthio)benzophenone.

5. The formulation of claim 2 wherein the compound of formula (I) is 4'-chloro-5-ethyl-2-(methylthio)benzophenone.

6. The formulation of claim 2 wherein the compound of formula (I) is 5-ethyl-2-(methylthio)benzophenone.

7. The method of claim 1 wherein the compound of formula (I) is 5-ethyl-4'-methyl-2-(methylthio)benzophenone.

8. The method of claim 1 wherein the compound of formula (I) is 5-ethyl-4'-fluoro-2-(methylthio)benzophenone.

9. The method of claim 1 wherein the compound of formula (I) is 4'-chloro-5-ethyl-2-(methylthio)benzophenone.

10. The method of claim 1 wherein the compound of formula (I) is 5-ethyl-2-(methylthio)benzophenone.

* * * * *

UNITED STATES PATENT OFFICE
CERTIFICATE OF CORRECTION

Patent No. 4,134,993              Dated January 16, 1979

Inventor(s) Delme Evans et al.

It is certified that error appears in the above-identified patent and that said Letters Patent are hereby corrected as shown below:

On the front page, Column 1, item [73] should read

--Assignee: Lilly Industries Limited, London, England--.

Signed and Sealed this

Fourth Day of December 1979

[SEAL]

Attest:

SIDNEY A. DIAMOND

Attesting Officer

Commissioner of Patents and Trademarks